United States Patent [19]

Nishihama et al.

[11] Patent Number: 5,961,995
[45] Date of Patent: Oct. 5, 1999

[54] COSMETIC COMPOSITION

[75] Inventors: Shuji Nishihama; Hiroshi Fukui, both of Yokohama, Japan

[73] Assignee: Shiseido Company, Ltd., Tokyo, Japan

[21] Appl. No.: 08/975,989

[22] Filed: Nov. 21, 1997

[30] Foreign Application Priority Data

Nov. 25, 1996 [JP] Japan ..................................... 8-329140

[51] Int. Cl.$^6$ ....................................................... A61K 7/02
[52] U.S. Cl. ............................ 424/401; 424/69; 424/70.1; 424/70.7; 424/70.9; 424/489; 514/844; 514/949; 514/951
[58] Field of Search ..................................... 424/401, 489, 424/69, 70.1, 70.7, 70.9; 514/844, 949, 951

[56] References Cited

U.S. PATENT DOCUMENTS 5,679,361 10/1997 Pradier et al. ........................... 424/401
5,814,311 9/1998 Le Bras-Roulier et al. ............. 424/69

*Primary Examiner*—Jose' G. Dees
*Assistant Examiner*—Michael A. Williamson
*Attorney, Agent, or Firm*—Foley & Lardner

[57] ABSTRACT

A cosmetic composition containing a hollow spherically shaped aluminosilicate, which is superior in sebum absorption, moisture control, and feeling of use and which has a natural finish.

26 Claims, No Drawings

COSMETIC COMPOSITION

BACKGROUND OF THE INVENTION

1. Field of the Invention

The present invention relates to a cosmetic composition. More specifically, it relates to a cosmetic composition having improved sebum absorption, moisture control, and feeling of use.

2. Description of the Related Art

The sebum secreted from the skin functions to protect the skin from the outside world. On the other hand, the sebum mixed with the oil components, surfactant etc., of foundations etc., and becomes a cause of ruined makeup along with time. If a large amount of sebum is secreted, the sebum rises to the surface of the face and causing a greasy and shiny appearance. Therefore, cosmetics are being developed which blend a powder with a high oil absorption such as hydroxyapatite or zinc oxide to absorb a large amount of sebum and thereby improve the long-lastingness of the makeup and to prevent a greasy and shiny appearance caused by the sebum.

The hydroxyapatite used as a sebum absorbant, however, is superior in ability to absorb the sebum on the skin, but at the same time it has a high moisture absorption. Therefore, there is the problem of stickiness on the surface when moist or when the wearer is sweating. Further, zinc oxide has a small moisture absorption, but when it is formulated into cosmetics in large amount, it looks excessively white when it is applied to the skin and the appearance becomes unnatural in some cases. Furthermore, cosmetics containing hydroxyapatite and zinc oxide have the problem of a heavy spreadability at the time of application and a poor feeling in use.

SUMMARY OF THE INVENTION

Accordingly, the objects of the present invention are to solve the above problems in the prior art and to provide a cosmetic composition which is superior in absorption of sebum, moisture control, and feeling of use and further gives a natural final result.

In accordance with the present invention, there is provided a cosmetic composition comprising a hollow spherically shaped aluminosilicate therein.

DESCRIPTION OF THE PREFERRED EMBODIMENTS

To achieve the above object, the present inventors engaged in intensive studies and, as a result, found that, when hollow spherically shaped aluminosilicate is formulated into a cosmetic composition, it is possible to obtain a cosmetic composition improved in sebum absorption and moisture control and possible to obtain a good feeling of use and natural finishing, whereby the present invention has been completed.

That is, the cosmetic composition of the present invention is characterized by including a hollow spherically shaped aluminosilicate therein, together with any type of a cosmetic base.

Note that preferably the hollow spherically shaped aluminosilicate has a diameter of not more than 100 Å (angstrom). Further, the hollow spherically shaped aluminosilicate is preferably porous. Furthermore, the $SiO_2/Al_2O_3$ constituting the hollow spherically shaped aluminosilicate is preferably 1 to 2. Furthermore, as the hollow spherically shaped aluminosilicate, it is particularly preferable to use allophane.

Furthermore, the cosmetic composition of the present invention is characterized by the use thereof as facial use, makeup use, or hair use.

The present invention will now be explained in further detail.

The hollow spherically shaped aluminosilicate formulated into the cosmetic composition of the present invention can be obtained naturally in the form of a clay mineral of an amorphous aluminum silicate hydrate and can be obtained by removing the iron from weathered soils such as Kanuma soil, that is weathered volcanic ash or pumice.

As a typical aluminosilicate compound, kaolinite, mica, etc. may be mentioned. These compounds have a layered structure, and therefore, are inferior in spreadability and smoothness at the time of application compared with hollow spherically shaped aluminosilicate. Further, since kaolinite, mica, etc. do not have a hollow structure, no moisture control or moisture absorption can be obtained. Further, since the layered structure of such layered aluminosilicates acts to reflect light directly (i.e., regular reflection), an unnatural shine is provided when applied to the skin. Contrary to this, hollow spherically shaped aluminosilicates are superior in that they have the property of controlling and absorbing moisture due to their structure and have the effect of giving a smooth feeling at the time of application and a natural finish due to the scattering of light as a result of its spherical shape.

The hollow spherically shaped aluminosilicate used in the present invention is preferably 100 Å or less in diameter, preferably is porous, and more preferably has a ratio of the $SiO_2/Al_2O_3$ of 1 to 2. In particular, it is preferable that allophane be used as the hollow spherically shaped aluminosilicate.

The allophane particularly preferably used in the present invention may, for example, be obtained by removing the iron from soil by the method of O. P. Mehra et al (Clays and Clay Minerals 7, 317–327 (1960)).

Note that, in the present invention, the hollow spherically shaped aluminosilicate can be optionally used by making it hydrophobic by fatty acid soaps such as aluminum stearate, zinc myristate, waxes such as candelilla wax, carnauba wax, and silicone oils such as methyl polysiloxane.

The amount of the hollow spherically shaped aluminosilicate formulated into the cosmetic composition of the present invention differs depending on the type, shape, etc. of the cosmetic composition used, but preferably is 0.1 to 98% by weight, more preferably 0.5 to 80% by weight. When the amount formulated is less than 0.1% by weight, the desired effect can no longer be obtained in some cases, while even if over 98% by weight is used, no further rise in effect can be observed.

The cosmetic composition of the present invention may, for example, take the form of a powder, cake, pencil, stick, ointment, liquid, etc. Specifically, facial cosmetics such as lotion, an emulsion (or milky lotion), a cream, makeup cosmetic such as foundation, lipstick, eye shadow, rouge, eyeliner, nail enamel, mascara, hair cosmetics such as hair treatment, hair liquid, setting lotions may be mentioned.

Note that the cosmetic composition of the present invention may contain, in addition to the above-mentioned essential components, various types of components normally used in cosmetics within a range not impairing the effect of the present invention. For example, solid and semisolid oils such as vaseline, lanolin, ceresin, carnauba wax, candelilla wax, higher fatty acids, higher alcohol; liquid oils such as squalane, liquid paraffin, ester oils, triglycerides; oils such as silicone oils; humectants such as sodium hyaluronate, glycerine; surfactants such as cationic surfactants, non-ionic surfactants; antioxidants; UV absorbants; UV blockers; dyes; pigments; preservatives; fragrances; activators; etc. may be suitably formulated thereinto.

EXAMPLES

The present invention will now be further illustrated by, but is by no means limited to, the following Examples. Note that the amounts are percents by weight unless otherwise specified.

Example 1 and Comparative Example 1

First, baby powder was prepared according to the formulation shown in Table 1 and evaluated as to moisture absorption. The amount of moisture absorbed was measured by the following method.

Measurement of Amount of Moisture Absorption

The moisture absorption of the baby powder was evaluated by placing baby powder dried at 105° C. in a desiccator adjusted to a relative humidity of 93% and a desiccator containing a silica gel, placed in a dried state, and adjusted to a relative humidity of 43% and measuring the amount of moisture absorbed by 100 g of the baby powder after 3 hours.

TABLE 1

|  | Example 1 | Comparative Example 1 |
| --- | --- | --- |
| (1) Hollow spherically shaped aluminosilicate | 93.0 | — |
| (2) Talc | — | 93.0 |
| (3) Zinc oxide | 3.0 | 3.0 |
| (4) Magnesium stearate | 4.0 | 4.0 |
| (5) Fragrance | q.s. | q.s. |
| Relative humidity 93% (g) | 7.32 | 0.16 |
| Relative humidity 43% (g) | 3.77 | 0.09 |
| In silica gel desiccator (g) | 1.73 | 0.11 |

Preparation

The components (3) and (4) were added to the component (1) or (2) and mixed well, then the component (5) was sprayed on and mixed uniformly. The mixture was pulverized by a pulverizer, then passed through a sieve to obtain a baby powder.

Talc is a powder which absorbs a relatively large amount of moisture, and therefore, is often used for baby powder etc. As is clear from the above results, a comparison of Example 1 and Comparative Example 1 shows that Example 1 exhibits a higher moisture absorption power. Further, while Comparative Example 1 exhibits the same amount of moisture absorption without regard to the outside humidity, Example 1 absorbs more moisture the higher the outside humidity. This suggests that hollow spherically shaped aluminosilicates have a moisture controlling function.

Example 2 and Comparative Example 2

Next, a powdery foundation was prepared according to the formulation of Table 2 and studied as to the amount of oil absorption. Note that the amount of oil absorption was measured by the following method.

Measurement of Oil Absorption 5 g of the powdery foundation was taken on a plate. As an oil component similar to sebum, squalane was dropped on the plate, then a spatula was used to mix the foundation until it coalesced as a single mass. The amount of the squalane dropped up to this time was used as the amount of oil absorbed by the foundation.

TABLE 2

|  | Example 2 | Comparative Example 2 |
| --- | --- | --- |
| (1) Talc | 15.0 | 15.0 |
| (2) Mica | 30.0 | 30.0 |
| (3) Hollow spherically shaped aluminosilicate | 15.0 | — |
| (4) Kaolin | — | 15.0 |
| (5) Titanium dioxide | 15.0 | 15.0 |
| (6) Titanium mica | 3.0 | 3.0 |
| (7) Zinc stearate | 1.0 | 1.0 |
| (8) Nylon powder | 5.0 | 5.0 |
| (9) Red ferrous oxide | 1.0 | 1.0 |
| (10) Yellow ferrous oxide | 3.0 | 3.0 |
| (11) Black ferrous oxide | 0.2 | 0.2 |
| (12) Squalane | 6.0 | 6.0 |
| (13) Lanolin acetate | 1.0 | 1.0 |
| (14) Octyldecyl myristate | 2.0 | 2.0 |
| (15) Sorbitan diisooctanate | 2.0 | 2.0 |
| (16) Sorbitan monoleate | 0.5 | 0.5 |
| (17) Preservative | q.s. | q.s. |
| (18) Antioxidant | q.s. | q.s. |
| (19) Fragrance | q.s. | q.s. |
| Oil absorption (g/100 g) | 42.5 | 38.8 |

Preparation

The components (1) and (9) to (11) were mixed by a Henschel mixer, followed by adding (2) to (8) and mixing well together with the mixture, then (13) to (18) were heated to melt with each other at 70° C., then added and mixed in. The mixture was then pulverized by a 5 HP pulverizer (Hosokawa Micron), then shaped into a dish to obtain the powdery foundation.

Kaolin is a powder generally used in cosmetics due to its high adhesion to the skin and higher oil absorption. As is clear from the above results, however, a comparison of Example 2 and Comparative Example 2 suggests that Example 2 has a higher oil absorption of squalane and is superior in skin oil absorption ability.

Example 3 and Comparative Example 3

A Dual-purpose Foundation

Next, foundation was prepared according to the formulation of Table 3 and evaluated as to the amount of oil absorption and the whitening at the time of use. The amount of oil absorption was evaluated according to the above method, while the whitening at the time of use was evaluated by scoring the Examples and Comparative Examples by a sensory evaluation by a panel of six members by the following criteria and using the average score for each Example and Comparative Example.

Criteria of Evaluation

Whitening

5: Does not seem white—natural appearance

4: If having to say one way or the other, does not seem white, but natural

3: Can't say either way

2: Looks white and unnatural

1: Extremely looks white and unnatural

TABLE 3

|  | Example 3 | Comparative Example 3 |
|---|---|---|
| (1) Silicone treated talc | 19.0 | 19.0 |
| (2) Silicone treated mica | 40.0 | 40.0 |
| (3) Silicone treated titanium dioxide | 5.0 | 5.0 |
| (4) Silicone treated hollow spherically shaped aluminosilicate | 15.0 | — |
| (5) Silicone treated zinc oxide | — | 15.0 |
| (6) Silicone treated red iron oxide | 1.0 | 1.0 |
| (7) Silicone treated yellow iron oxide | 3.0 | 3.0 |
| (8) Silicone treated black iron oxide | 0.2 | 0.2 |
| (9) Zinc stearate | 0.1 | 0.1 |
| (10) Nylon powder | 2.0 | 2.0 |
| (11) Squalane | 4.0 | 4.0 |
| (12) Solid paraffin | 0.5 | 0.5 |
| (13) Dimethyl polysiloxane | 4.0 | 4.0 |
| (14) Glycerol triisooctanate | 5.0 | 5.0 |
| (15) Octyl methoxycinnamate | 1.0 | 1.0 |
| (16) Preservative | q.s. | q.s. |
| (17) Antioxidant | q.s. | q.s. |
| (18) Fragrance | q.s. | q.s. |
| Oil absorption (g/100 g) | 33.2 | 32.2 |
| Average score | 4.0 | 2.8 |

Preparation

The components (1) to (10) were mixed in a Henschel mixer, then (11) to (18) heated to melt with each other at 70° C. were added and mixed together. The mixture was then pulverized by a 5 HP pulverizer (Hosokawa Micron) and shaped in a dish to obtain the foundation.

Zinc oxide is a powder generally used as solidifying sebum. When formulated in a large amount, however, there is the problem of white appearance when applied to the skin. As clear from the above results, however, a comparison of Example 3 and Comparative Example 3 suggests, there is no difference in the amounts of oil absorption, while the present invention does not cause white appearance and is superior in feeling of use in terms of the scores in the sensory evaluation.

Example 4 and Comparative Example 4

Next, an emulsified foundation was prepared according to the formulation of Table 4 and evaluated as to the amount of oil absorption and the stickiness at the time of use. The amount of oil absorption was evaluated by the above method, while the stickiness at the time of use was evaluated by scoring the Examples and Comparative Examples by a sensory evaluation by a panel of six members by the following criteria and using the average score for each Example and Comparative Example.

Criteria of Evaluation

Stickiness

5: Not sticky—extremely satiny

4: If having to say one way or the other, satiny

3: Can't say either way

2: Somewhat sticky

1: Extremely sticky

TABLE 4

|  | Example 4 | Comparative Example 4 |
|---|---|---|
| (1) Ion exchange water | 60.9 | 60.9 |
| (2) Dispersant | 0.1 | 0.1 |
| (3) Dipropylene glycol | 5.0 | 5.0 |
| (4) Preservative | q.s. | q.s. |
| (5) Polyoxyethylene modified dimethyl polysiloxane | 4.0 | 4.0 |
| (6) Decamethyl cyclopentasiloxane | 12.0 | 12.0 |
| (7) Liquid paraffin | 5.0 | 5.0 |
| (8) Hollow spherically shaped aluminosilicate | 5.0 | — |
| (9) Hydroxyapatite | — | 5.0 |
| (10) Sericite | 5.36 | 5.36 |
| (11) Titanium dioxide | 8.32 | 8.32 |
| (12) Yellow iron oxide | 0.8 | 0.8 |
| (13) Red iron oxide | 0.36 | 0.36 |
| (14) Black iron oxide | 0.16 | 0.16 |
| (15) Fragrance | q.s. | q.s. |
| Oil absorption (g/100 g) | 40.2 | 39.7 |
| Average score | 3.8 | 2.7 |

Preparation

The components (1) to (4) were heated and stirred at 70° C., then (8) to (14) were added and dispersed. The resultant mixture was added to (5) to (7) heated in advance to 70° C., then the mixture emulsified and dispersed. Next, the mixture was stirred and cooled to room temperature, then (14) was added to obtain the desired emulsified foundation.

Hydroxyapatite is a powder generally used as a sebum absorbant. While superior in sebum absorption power on the skin, there is the problem that since there is also moisture absorption, the surface becomes sticky when moist or when the wearer is sweating. As clear from the above results, a comparison of Example 4 and Comparative Example 4 shows that, while there is no difference in terms of the amount of oil absorption, stickiness was caused in Comparative Example 4, while it was suppressed in Example 4, and therefore, a superior feeling in use was obtained.

Example 5 and Comparative Example 5

Next, an oily stick foundation was prepared according to the formulation of Table 5 and evaluated as to stickiness at the time of use. This was evaluated by scoring the Examples and Comparative Examples by a sensory evaluation by a panel of six members by the following criteria and using the average score for each Example and Comparative Example.

Criteria of Evaluation

Roughness

5: Not rough—extremely smooth

4: If having to say one way or another, smooth

3: Can't say either way

2: Somewhat rough

1: Extremely rough

TABLE 5

|  | Example 5 | Comparative Example 5 |
|---|---|---|
| (1) Hollow spherically shaped aluminosilicate | 13.0 | — |
| (2) Zinc oxide | — | 13.0 |
| (3) Titanium oxide | 7.0 | 7.0 |

TABLE 5-continued

|  | Example 5 | Comparative Example 5 |
|---|---|---|
| (4) Kaolin | 20.0 | 20.0 |
| (5) Talc | 2.0 | 2.0 |
| (6) Mica | 3.3 | 3.3 |
| (7) Red iron oxide | 1.0 | 1.0 |
| (8) Yellow iron oxide | 3.0 | 3.0 |
| (9) Black iron oxide | 0.2 | 0.2 |
| (10) Solid paraffin | 3.0 | 3.0 |
| (11) Microcrystalline wax | 7.0 | 7.0 |
| (12) Vaseline | 15.0 | 15.0 |
| (13) Dimethyl polysiloxane | 3.0 | 3.0 |
| (14) Squalane | 5.0 | 5.0 |
| (15) Isopropyl palmitate | 17.0 | 17.0 |
| (16) Antioxidant | q.s. | q.s. |
| (17) Fragrance | q.s. | q.s. |
| Average score | 4.2 | 3.5 |

Preparation

The components (10) to (16) were dissolved at 85° C., followed by adding thereto the components (1) to (9) thereto and mixed by a disperser, then dispersed by a colloid mill. (17) was added thereto, then the mixture was deaerated and poured into a container at 70° C. and cooled to obtain the desired product.

As is clear from the above results, in general, even if the powders such as the zinc oxide is blended in the cosmetic composition, since the particles are small in size, no roughness occurs during the use of the product, but according to Example 5 in which the hollow spherically shaped aluminosilicate is blended, it is suggested that it is possible to obtain a cosmetic composition further suppressed in roughness in use.

The preferable Examples of the formulations of the present invention will now be shown. Note that the present invention is not limited to these formulations and also that the amounts formulated are all % by weight.

Formulation 1: Face Powder

| (1) Hollow spherically shaped aluminosilicate | 75.0 wt % |
|---|---|
| (2) Titanium oxide | 3.0 |
| (3) Kaolin | 5.0 |
| (4) Zinc myristate | 5.0 |
| (5) Magnesium carbonate | 5.0 |
| (6) Sericite | 7.0 |
| (7) Coloring pigment | q.s. |
| (8) Fragrance | q.s. |

Preparation

The components (1) and (7) were mixed by a blender, followed by adding (2) to (6) and mixed well together, then (8) was sprayed and the resultant mixture mixed uniformly. This was pulverized by a pulverizer, then passed through a sieve to obtain the desired substance.

| (1) Hollow spherically shaped aluminosilicate | 5.0 wt % |
|---|---|
| (2) Lithol rubine B (Red # 201) | 0.6 |
| (3) Lithol rubine BCA (Red # 202) | 1.0 |
| (4) Lake red C (Red # 203) | 0.2 |
| (5) Candelilla wax | 9.0 |
| (6) Solid paraffin | 8.0 |

-continued

| (7) Beeswax | 5.0 |
|---|---|
| (8) Carnauba wax | 5.0 |
| (9) Lanolin | 11.0 |
| (10) Castor oil | 25.0 |
| (11) Cetyl 2-ethylhexanoate | 20.0 |
| (12) Isopropyl myristic acid ester | 10.0 |
| (13) Antioxidant | q.s. |
| (14) Fragrance | q.s. |

Preparation

Part of the component (10) was added to the components (1) to (3) and the resultant mixture processed by rollers (pigment portion). Separately, (4) was dissolved in part of (10) (dye portion). (5) to (14) were heated to 90° C. to melt with each other, then the pigment portion and dye portion were added and dispersed uniformly by a homogenizer. After dispersion, the resultant mixture was filled in a predetermined container to obtain the desired oily lipstick.

Formulation 3: Sunscreen Agent

| (1) Hollow spherically shaped aluminosilicate | 5.0 wt % |
|---|---|
| (2) Ion exchange water | 54.95 |
| (3) 1,3-butylene glycol | 7.0 |
| (4) Disodium edetate | 0.05 |
| (5) Triethanolamine | 1.0 |
| (6) Oxybenzone | 2.0 |
| (7) Octyl p-methoxycinnamate | 5.0 |
| (8) Squalane | 10.0 |
| (9) Vaseline | 5.0 |
| (10) Stearyl alcohol | 3.0 |
| (11) Stearic acid | 3.0 |
| (12) Glycerol monostearate | 3.0 |
| (13) Polyethyl acrylate | 1.0 |
| (14) Antioxidant | q.s. |
| (15) Preservative | q.s. |
| (16) Fragrance | q.s. |

Preparation

The components (2) to (5) were heated to 70° C. to melt with each other, followed by adding (1) to this and made to sufficiently disperse. The components (6) to (16) heated to melt with each other were added to this, then the mixture emulsified and dispersed using a homogenizer. Next, the resultant mixture was agitated and cooled to room temperature to obtain a desired sunscreen agent.

Formulation 4: W/O Type Sunscreen Agent

| (1) Ion exchange water | 38.3 wt % |
|---|---|
| (2) 1,3-butylene glycol | 5.0 |
| (3) Silicone treated hollow spherically shaped aluminosilicate | 3.0 |
| (4) Octyl p-methoxycinnamate | 5.0 |
| (5) Oxybenzone | 3.0 |
| (6) 4-tert-4'-methoxybenzoyl methane | 1.0 |
| (7) Squalane | 40.0 |
| (8) Glycerol diisostearate | 3.0 |
| (9) Organic modified montmorillonite | 1.5 |
| (10) Preservative | q.s. |
| (11) Fragrance | q.s. |

Preparation

The components (4) to (11) were heated to 70° C. to melt with each other, followed by adding the component (3) and made to sufficiently disperse. (1) and (2) heated to melt with each other were added thereto and the resultant mixture was emulsified and dispersed using a homogenizer. Next, the mixture was stirred and cooled to room temperature to obtain the desired W/O type sunscreen agent.

| (1) Kaolin | 19.0 wt % |
|---|---|
| (2) Hollow spherically shaped aluminosilicate | 5.0 |
| (3) Red oxide of iron | 0.3 |
| (4) Lithol rubine BCA | 0.5 |
| (5) Ceresin | 15.0 |
| (6) Vaseline | 20.0 |
| (7) Liquid paraffin | 25.0 |
| (8) Isopropyl myristic acid ester | 15.0 |
| (9) Antioxidant | q.s. |
| (10) Fragrance | q.s. |

Preparation

The components (1) to (4) were added to part of the component (7) and the resultant mixture was processed by rollers (pigment portion). (5) to (10) were heated to 90° C. to melt with each other, the pigment portion was added, and the mixture was dispersed uniformly by a homomixer. After dispersion, the mixture was filled in a predetermined container to obtain the desired rouge.

As explained above, according to the present invention, by formulating a hollow spherically shaped aluminosilicate into a cosmetic composition, it is possible to obtain a cosmetic composition having a high sebum absorption, moisture control, a good feeling in use, and a natural finish.

We claim:

1. A cosmetic composition comprising 0.1 to 98% by weight of a hollow spherically shaped aluminosilicate therein, wherein the aluminosilicate comprises a composition having the formula $Al_2O_3/SiO_2$.

2. A cosmetic composition as claimed in claim 1, wherein said hollow spherically shaped aluminosilicate has a diameter of not more than 100 Å.

3. A cosmetic composition as claimed in claim 1, wherein said hollow spherically shaped aluminosilicate is porous.

4. A cosmetic composition as claimed in claim 1, wherein the ratio of the $SiO_2/Al_2O_3$ constituting the hollow spherically shaped aluminosilicate is 1 to 2.

5. A cosmetic composition as claimed in claim 1, wherein said hollow spherically shaped aluminosilicate is allophane.

6. A cosmetic composition as claimed in claim 1, wherein the cosmetic composition is for facial use.

7. A cosmetic composition as claimed in claim 1, wherein the cosmetic composition is for makeup use.

8. A cosmetic composition as claimed in claim 1, wherein the cosmetic composition is for hair use.

9. A cosmetic composition as claimed in claim 2, wherein said hollow spherically shaped aluminosilicate is porous.

10. A cosmetic composition as claimed in claim 2, wherein the ratio of the $SiO_2/Al_2O_3$ constituting the hollow spherically shaped aluminosilicate is 1 to 2.

11. A cosmetic composition as claimed in claim 3, wherein the ratio of the $SiO_2/Al_2O_3$ constituting the hollow spherically shaped aluminosilicate is 1 to 2.

12. A cosmetic composition as claimed in claim 2, wherein said hollow spherically shaped aluminosilicate is allophane.

13. A cosmetic composition as claimed in claim 3, wherein said hollow spherically shaped aluminosilicate is allophane.

14. A cosmetic composition as claimed in claim 4, wherein said hollow spherically shaped aluminosilicate is allophane.

15. A cosmetic composition as claimed in claim 2, wherein the cosmetic composition is for facial use.

16. A cosmetic composition as claimed in claim 3, wherein the cosmetic composition is for facial use.

17. A cosmetic composition as claimed in claim 4, wherein the cosmetic composition is for facial use.

18. A cosmetic composition as claimed in claim 5, wherein the cosmetic composition is for facial use.

19. A cosmetic composition as claimed in claim 2, wherein the cosmetic composition is for makeup use.

20. A cosmetic composition as claimed in claim 3, wherein the cosmetic composition is for makeup use.

21. A cosmetic composition as claimed in claim 4, wherein the cosmetic composition is for makeup use.

22. A cosmetic composition as claimed in claim 5, wherein the cosmetic composition is for makeup use.

23. A cosmetic composition as claimed in claim 2, wherein the cosmetic composition is for hair use.

24. A cosmetic composition as claimed in claim 3, wherein the cosmetic composition is for hair use.

25. A cosmetic composition as claimed in claim 4, wherein the cosmetic composition is for hair use.

26. A cosmetic composition as claimed in claim 5, wherein the cosmetic composition is for hair use.

* * * * *